United States Patent [19]
Norton et al.

[11] Patent Number: 5,880,474
[45] Date of Patent: Mar. 9, 1999

[54] MULTI-ILLUMINATION-SOURCE FLOW PARTICLE ANALYZER WITH INTER-LOCATION EMISSIONS CROSSTALK CANCELATION

[75] Inventors: Pierce Owen Norton, Morgan Hill; Robert A. Hoffman, Livermore, both of Calif.

[73] Assignee: Becton Dickinson and Company, Franklin Lakes, N.J.

[21] Appl. No.: 920,382

[22] Filed: Aug. 29, 1997

[51] Int. Cl.[6] .............................. G01J 1/58; G01N 21/25; G01N 33/48
[52] U.S. Cl. .................................... 250/458.1; 250/459.1; 356/317
[58] Field of Search .............................. 250/458.1, 459.1, 250/461.2, 358.1, 226; 356/317, 39, 411; 436/52; 422/82.08; 209/576

[56] References Cited

U.S. PATENT DOCUMENTS

| | | | |
|---|---|---|---|
| 4,867,908 | 9/1989 | Recktenwald et al. | 252/408.1 |
| 5,682,038 | 10/1997 | Hoffman | 250/458.1 |

OTHER PUBLICATIONS

James C. S. Wood et al.: "Dual Laser Excitation Flow Cytometry: The State-of-the-Art". Book entitled Flow Cytometry: Advanced research and Clinical Applications, vol. 1, 1989 Boca Raton, Florida, pp. 6–7, 18–25, Illumination and Optics Components, pp. 28–33, Analogue Signal Processing, Data Acquisition, and Display.

Ger Van Den Engh et al.: "Parallel Processing Data Acquisition System for Multilaser Flow Cytometry and Cell Sorting." Cytometry vol. 10, pp. 282–293 (1989), 1989 Alan R. Liss, Inc., see the whole document.

George B. J. Dubelaar.: "Optical Plankton analyser: A Flow Cytometer for Plankton Analysis, II: Specifications 1" Cytometry vol. 10, pp. 529–539 (1989), 1989 Alan R. Liss, Inc., see the whole document.

R. D. Hiebert et al.: "Electronic for Flow Cytometers and Sorters" Flow Cytometery: Instrumentationa DN Data Analysis vol. 4, pp. 129–162, Copyright 1985 by Academic Pres Inc. (London) Ltd., ISBN 0–12–712150–1, see the whole document.

Howard M. Shapiro et al.: "Cytomat–R: A Computer–Controlled Multiple Laser Source Multiparameter Flow Cytophotometer System" The Journal of Histochemistry and Cytochemistry, vol. 25, No. 7, pp. 836–844, 1977 Copyright 1977 by The Histochemical Society, Inc., Printed in the U.S.A., see the whole document.

*Primary Examiner*—Edward P. Westin
*Assistant Examiner*—Richard Hanig
*Attorney, Agent, or Firm*—Allen W. Wark; Eric M. Lee; Susan A. Capello

[57] ABSTRACT

A multi-laser flow-cytometry system provides for inter-location emissions crosstalk cancellation, through either pulse subtraction or gating, to avoid false triggering based on shadow (pre- and post-) pulses that occur when red-excited red emissions are detected by a photodetector arranged to detect blue-excited red emissions. This overcomes a problem of undercounting of counting beads that led to misdeterminations of cell counts when blue-excited red fluorescence detections were used as a trigger. The approach also provides for more accurate quantitative data regarding fluorochrome emissions amplitudes.

13 Claims, 3 Drawing Sheets

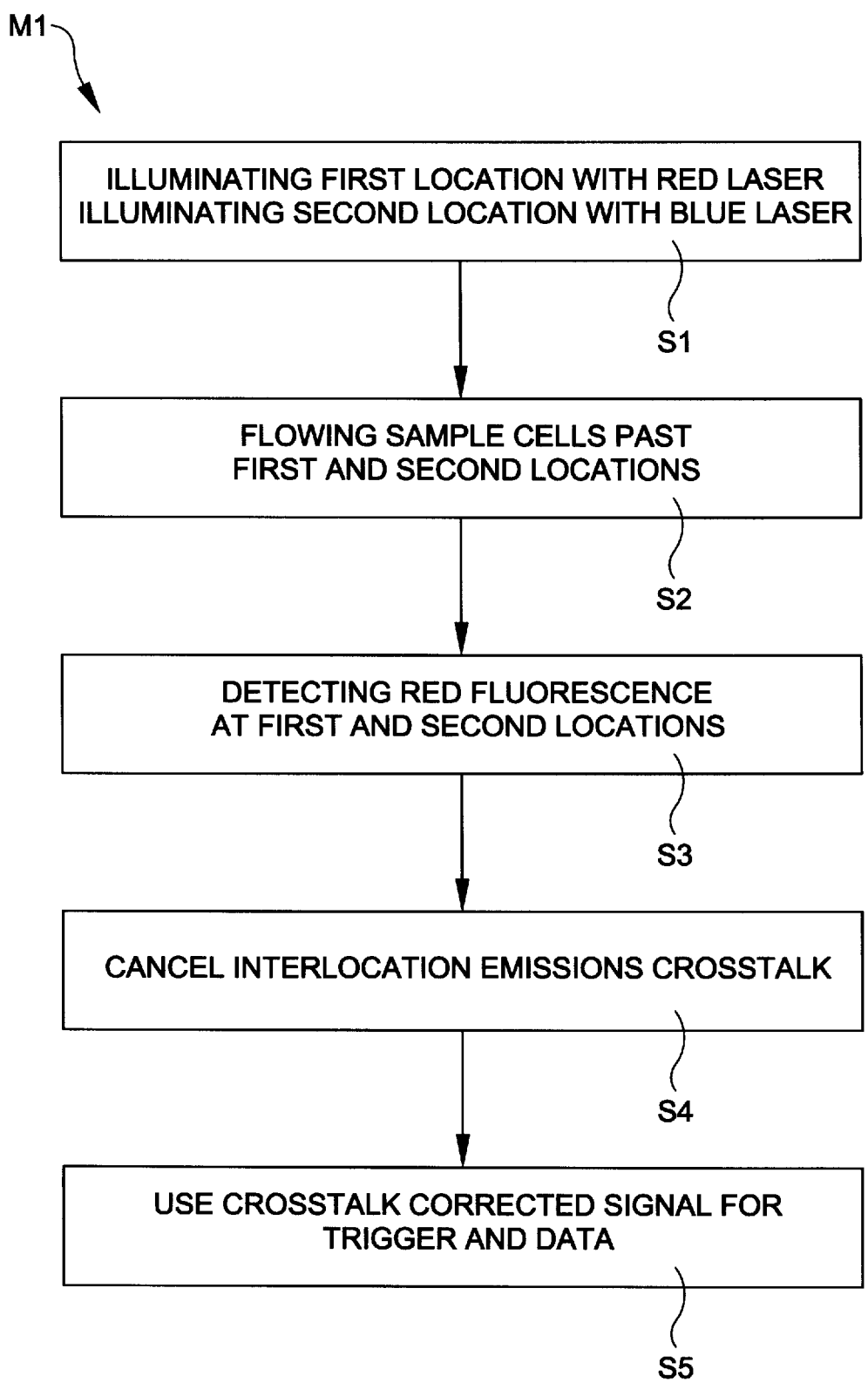

MULTI-ILLUMINATION-SOURCE FLOW PARTICLE ANALYZER WITH INTER-LOCATION EMISSIONS CROSSTALK CANCELATION

BACKGROUND OF THE INVENTION

The present invention relates to analytical instruments and, more particularly, to flow particle analysis such as used in cytometry. A major objective of the present invention is to reduce false triggering in multi-laser flow cytometry systems.

A typical single-laser flow cytometry system includes a flow subsystem for flowing a particle stream along a flow path, a blue laser illumination source for illuminating a location along the flow path, several photodetectors for detecting light modulations (e.g., due to emissions, absorption, and scattering) at the illuminated flow path location, analog pulse-processing circuitry for processing the photodetector outputs, a digitizer, and a digital data processor (computer) for analyzing digitized detector data to characterize the particle stream.

The photodetectors can include a detector for forward-scattered light, a detector for side-scattered light, a green fluorescence detector, a yellow fluorescence detector, and a red fluorescence detector. The scatter detectors can be used to detect the presence and indicate the size of a particle at the illuminated location. The fluorescence detectors can be used to distinguish three fluorochromes: a blue-excited green fluorochrome (e.g., FITC), a blue-excited yellow fluorochrome (e.g., RPE), and a blue-excited red fluorochrome (e.g., PerCP).

Attempts to provide for four-way fluorochrome distinctions using a single-laser system have proved difficult due to ambiguities caused by overlap of emissions spectra. Improved four-way fluorochrome distinction has been achieved using dual-laser systems. A typical dual-laser system adds a red laser illumination source to illuminate a second location along the flow path. The additional laser allows a red-excited (and not blue-excited) red fluorochrome (e.g., APC) to be distinguished from a blue-excited (and not red-excited) red fluorochrome (e.g., PerCP). Each of these red fluorochromes are readily distinguished from the blue-excited green fluorochrome and the blue-excited yellow fluorochrome. Research and development is ongoing on extending the multi-laser approach to provide for greater than four-way fluorochrome distinctions.

The photodetector outputs not only serve as the sources of data to be analyzed, but also determine what portions of the data are to be analyzed. To this end, one or a combination of photodetector outputs can be used to derive a trigger signal that activates processing, including digitization. In the absence of a trigger signal, signals from the photodetector outputs are gated. Peak and hold circuits and subsequent digitizers are examples of analog components that can require recovery time after processing a signal. Therefore, limiting amplification of uninteresting signals can help ensure appropriate processing of interesting data. Furthermore, gating limits the amount of data that must be digitized, processed and stored.

In general, a trigger determines a window of time within which interesting data is expected and, therefore, data processing is activated. Often, a trigger is initiated when a scatter detector output crosses a threshold—indicating with a high level of certainty that a particle is in the flow-path location corresponding to the detector. The fluorescent particle detector outputs can then be amplified, digitized, and processed to identify any fluorochromes in the particle—so that the particle (which may be inherently fluorescent or tagged with one or more fluorescent markers) can be characterized.

Accurate triggering is important. A false negative, i.e., no trigger when a particle (or alternative indicator of interesting data) is present, causes a loss of valuable data. A false positive, a trigger when no particle or alternative indicator of interesting data is present, burdens the analog and digital processing systems. Furthermore, many flow analyzers fail to process new events while processing data relating to the supposed event associated with a trigger. During this "dead time", interesting events can avoid detection, causing a loss of interesting data. Thus, both false positives and false negatives can cause a loss of data required for an accurate analysis. It should be noted that the data loss is often systematic in that certain types of interesting events are more likely to be discarded than others. Thus false triggering can bias the analysis.

In a single-laser system, processing dead time after a trigger can be on the order of the time it takes a particle to traverse the laser beam where it intersects the flow path; this may be a couple of microseconds. In a dual-laser system, the processing dead time can be on the order of the transit time a particle takes in moving from the upstream detection location to the downstream detection location; this may be seven to twenty-five microseconds. More generally, in a multi-laser system, the dead time is on the order of the transit time between the first and last detection locations. Thus, the penalty in lost interesting data for false positive triggers in a dual- or other multi-laser system can be substantial.

Processing dead time in a multi-laser system can be reduced by minimizing the separation of the illumination locations. The cost of this solution is increased interlocation emissions crosstalk between illumination locations. In other words, light emitted or scattered at a first illumination location can leak to a second location so that it is detected by photodetectors arranged to detect light at the second location. In particular, red-excited red fluorescence can be detected by a detector arranged to detect blue-excited red fluorescence. This can lead to a false indication of a blue-excited red fluorochrome when there is no such material at the location illuminated by the blue laser. The converse false indication of a red-excited red fluorochrome at the flow-path location illuminated by the blue laser can also occur.

In the case a particle stimulates fluorescent emission at a location upstream of the location indicated by the detection circuitry, the false indication is referred to as a "pre-pulse". In the case a particle stimulates fluorescent emission at a location downstream of the location indicated by the detection circuitry, the false indication is referred to as a "post-pulse". Herein, the term "shadow pulse" is used to encompass both pre-pulses and post-pulses.

In general, a shadow pulse associated with a trigger signal is outside of the trigger window. For example, in a dual-laser system that triggers on the upstream illumination location, the output of a detector for the downstream illumination location is not processed until the triggering particle has had time to reach the downstream location. The pre-pulse generated concurrently with the trigger is ignored.

However, a trigger particle might fail to trigger if it passes the upstream trigger location during a dead time. If it causes a strong modulation of light when it reaches the downstream illumination location, the resulting post-pulse could result in a trigger. Since the downstream photodetector output would be ignored, there would be no indication that the trigger was false. Hence, a penalty in processing activity and dead time would ensue with no offsetting acquisition of useful data. In fact, there would be a false indication of a non-fluorescent particle; such "selective elimination" would distort the determination of the sample composition.

Evaluating the lymphocyte content of a blood sample is an example of an application in which a shadow pulse could induce a false trigger. The blood sample can be lysed and unwashed, so that sample is filled with uninteresting particles, i.e., debris. The debris particles can be so numerous relative to the white cells of interest that particle presence is not a sufficiently selective criterion for triggering. In fact, the debris can be sufficiently dense that scattering detections are practically continuous, rendering the scatter detectors essentially useless for such a sample.

Accordingly, it is appropriate to tag white cells with a fluorochrome that can be used as a trigger. From a sample preparation standpoint, it can be most convenient to tag white blood cells with blue-excited red fluorochrome, e.g., PerCP, which thus becomes the triggering fluorochrome. Other fluorochrome tags are attached to specific respective lymphocytes.

Fluorochrome detections tend to be much weaker than scatter detections; as a result, trigger thresholds for fluorochrome triggering must be set near the noise floor for the respective fluorochrome detector. A (e.g., blue-excited-red indication) shadow pulse at the trigger location, resulting from a (e.g., red-excited red) fluorochrome at the non-trigger location, can be sufficient to cross the trigger threshold at the location.

The options appear to be to accept the false triggering, to avoid samples where such false triggering is likely to arise, or to develop a scheme to minimize such false triggering where it is otherwise likely to arise. Clearly, the last option is the most attractive.

SUMMARY OF THE INVENTION

The present invention provides a multi-laser system with post-detection cancellation of interlocation emissions crosstalk. The multi-laser system includes a flow subsystem for flowing particles along a flow path, at least two lasers with different spectral distributions illuminating different locations along the flow path, and respective detectors for detecting illumination modulations at the two locations. At least one of the detectors is capable of detecting an event at its respective location causing interlocation emissions crosstalk at a detector at a different location. The invention adds means for canceling the indication of crosstalk generated by the detector responding to the optical crosstalk. In the preferred embodiments, the cross-talking detections are of fluorescence—typically red fluorescence.

Interlocation emissions crosstalk cancellation can be performed by subtracting a scaled version of the main indicator of the event causing the crosstalk from the output of the detector detecting the crosstalk. Conveniently, the subtraction can be conducted along with other subtractions designed to cancel other forms of crosstalk, e.g., intralocation emissions crosstalk due to overlap in the emissions spectra of fluorochromes excited by the same laser, and excitation crosstalk due to overlap in excitation spectra. Interestingly, in many cases the subtrahend used for canceling crosstalk in excitation spectra and the subtrahend used for canceling optical crosstalk can be derived from the same event indicator; however, the latter is concurrent with the crosstalk-generating event indicator, while the former is time-shifted by the particle transit time between the illumination locations.

As an alternative to subtraction, the output of the detector responding to interlocation emissions crosstalk can be gated for the duration of the source event indicator, e.g., detection pulse. The gating blocks an interlocation emissions crosstalk detection pulse from a trigger path or from both a trigger and a data path. However, gating also eliminates any coincident indicator. Since the coincident indicator may constitute interesting information, this incidental elimination is considered undesirable. In addition, if gating is employed, it is necessary to determine which is the source indicator and which is the crosstalk indicator so that it is not the source indicator that is canceled. Since this source indicator is likely to be much stronger than the crosstalk indicator, the determination is not hard to make. However, extra circuitry and steps are required.

Where cancellation involves subtraction rather than gating, there is little penalty for mistaking a crosstalk indicator for a source indicator. Subtracting a fraction of a relatively weak crosstalk indication from a relatively strong source indicator would be unlikely to bring the latter below a triggering threshold. Furthermore, if the crosstalk indicator happens to be superimposed on an indication of a real event that is intended to be a trigger, the trigger indicator is likely to remain above threshold after cancellation of the crosstalk indicator.

Empirical data gathered from calibration runs can be used to determine the scaling required to derive the magnitude of a crosstalk indicator from the magnitude of the corresponding source indicator. If the crosstalk corrected output is to be used for particle characterization in addition to (or instead of) triggering, a term corresponding to the predicted crosstalk indicator should be subtracted from the detector output bearing the crosstalk indicator. However, if the crosstalk corrected output is not used for particle characterization, then it can be preferable to overcompensate for crosstalk to bias the system against false triggering.

The present invention provides clear advantages over prior art systems subject to uncompensated interlocation emissions crosstalk. The invention reduces false triggering and provides more accurate particle data. Furthermore, since the adverse affects of optical crosstalk are ameliorated by the invention, optical isolation is less critical. Thus, less separation is required between illumination locations. This, in turn, reduces dead time between event processings. Thus, more useful data can be collected so that a more accurate analysis results. These and other features and advantages of the invention are apparent from the description below with reference to the following drawings.

BRIEF DESCRIPTION OF THE DRAWINGS

FIG. 3 is a method performed using the system of FIG. 1 and incorporating the present invention.

DESCRIPTION OF THE PREFERRED EMBODIMENTS

Figure 1:
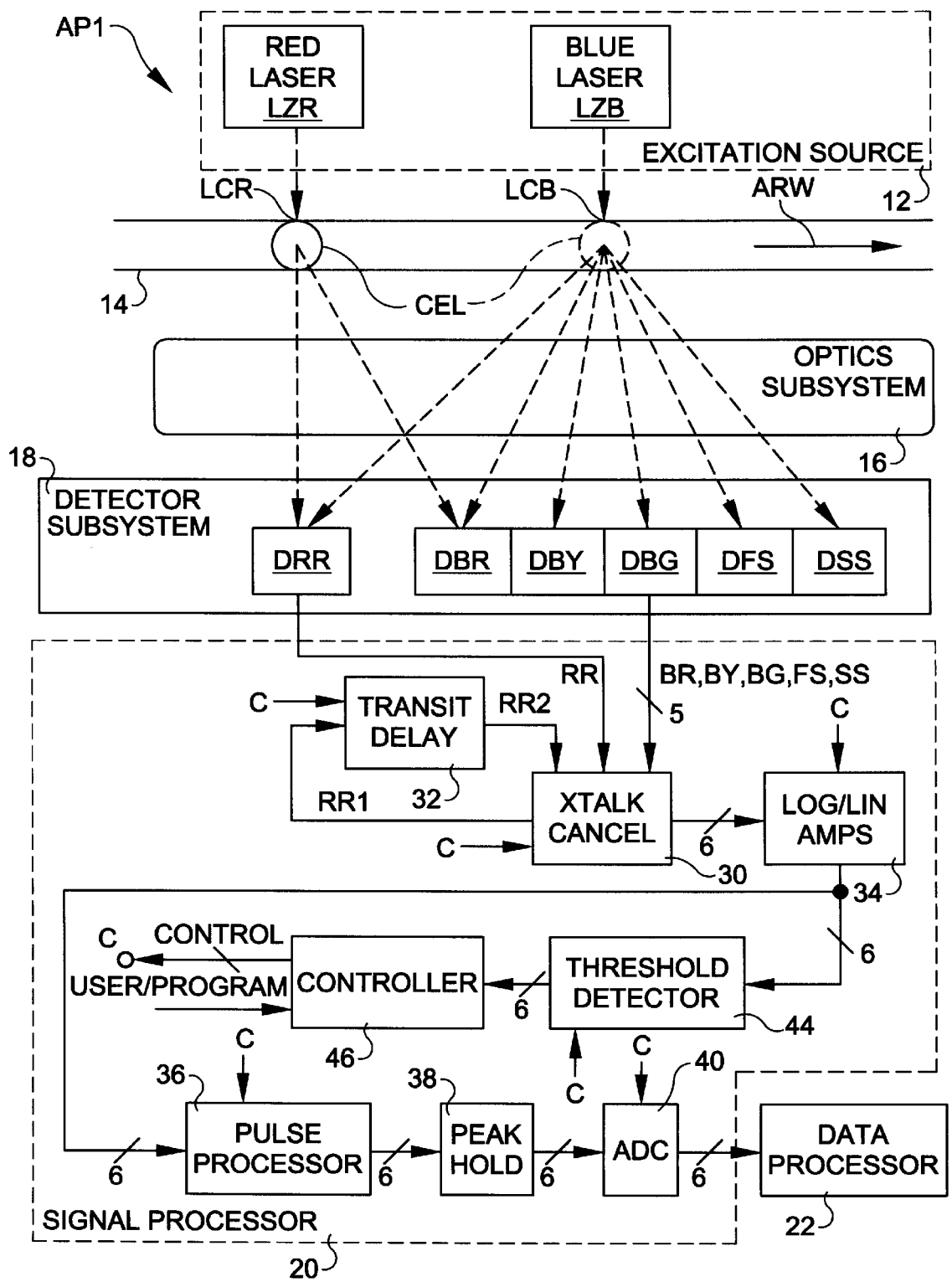
FIG. 1 is a schematic diagram of a flow cytometry system in accordance with the present invention.
Figure 2:
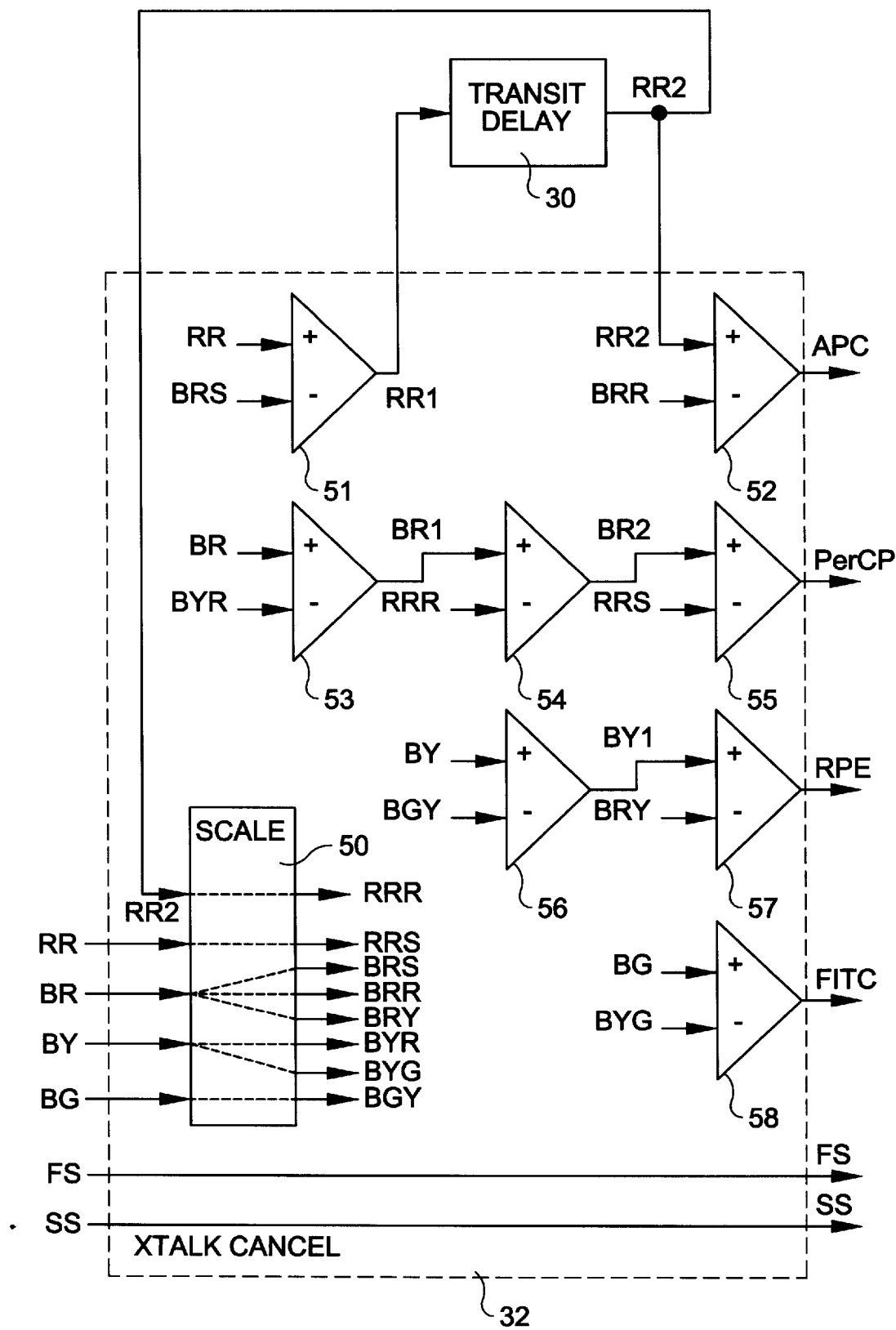
FIG. 2 is a schematic diagram of a crosstalk cancellation circuit of the system of FIG. 1.

In accordance with the present invention, a multi-laser flow cytometry system AP1 comprises an illumination subsystem 12, a flow subsystem 14, an optics subsystem 16, a detection subsystem 18, a signal processor 20, and a digital data processor 22, as shown in FIG. 1. Illumination subsystem 12 includes a 635 nanometer (nm) wavelength diode red laser LZR for illuminating a upstream location LCR and a 488 nm argon blue laser LZB for illuminating a location LCB 120 microns ($\mu$) downstream. Flow subsystem 14 causes a sample stream including a white cell CEL to flow in the direction of arrow ARW from location LCR to location LCB, traversing the distance in about 20 microseconds ($\mu$S).

The sample stream is a lysed and unwashed blood sample for which the lymphocyte distribution is of interest. The sample includes count beads that are used to determine the original sample volume equivalent of sample run through the flow path. White cells are tagged with a blue-excited red fluorochrome PerCP, which is used as a pulse processing trigger. Various lymphocytes are marked with respective red-excited red, blue-excited yellow, and blue-excited green fluorochromes.

In the course of the invention, it was discovered that in a similarly configured system not incorporating the invention, the beads in a test sample were being undercounted; the undercounts led to erroneously high determinations of sample component concentrations. Further investigation indicated the system was triggering on pre-pulses generated by beads at location LCR; when a triggering bead reached the true trigger location LCB, the system aborted the event. The system was programmed to abort events that were too close together to be interpreted reliably. System AP1 applies the invention to solve this problem specifically, as well as minimize acquisition errors due to interlocation emission crosstalk more generally.

Detector subsystem 18 includes six photodetectors: a first photodetector DRR is arranged to detect red-excited red fluorescence, e.g., of APC, from location LCR; a second photodetector DBR is arranged to detect blue-excited red fluorescence, e.g., of PerCP, from location LCB; a third photodetector DBY is arranged to detect blue-excited yellow fluorescence, e.g., of RPE, from location LCB; a fourth photodetector DBG is arrange to detect blue-excited green fluorescence, e.g., of FITC, from location LCB; a fifth photodetector DFS is arranged to detect forward blue scatter at location LCB; and a sixth photodetector DSS is arranged to detect side blue scatter at location LCB. The photodetectors provide output signals RR, BR, BY, BG, FS, and SS, respectively, pulses along which indicate modulations in the light parameter the respective photodetector is designed to receive.

Optics subsystem 16 is designed to guide light of the proper spatial and spectral distribution to the appropriate one of the photodetectors, as indicated by the thicker dotted lines in FIG. 1. However, since optical isolation is not perfect, some crosstalk leaks between locations LCR and LCB as indicated by the thin dotted lines in FIG. 1. Of primary concern is crosstalk from red-excited red fluorescence that reaches blue-excited red photodetector PBR causing pre-pulses. The complementary crosstalk from blue-excited red to red-excited red photodetector DRR is also shown in FIG. 1; this crosstalk causes post-pulses. These two instances of interlocation emissions crosstalk are of concern because the resulting shadow pulses can falsely trigger pulse processing; furthermore they can cause data acquisition errors.

The photodetector output signals are processed by analog signal processor 20. Signal processor 20 includes the following components along the pulse data path: crosstalk cancellation circuit 30, transit delay circuit 32, an amplifier bank 34, pulse processor 36, peak holder 38, and analog-to-digital converter (ADC) 40. ADC 40 provides the output of signal processor 20 to data processor 22, which does the numerical analysis of the sample. In addition to the data path elements, a threshold detector 44 and a controller 46 provide for triggering and control signals for signal processor 20.

Crosstalk cancellation circuit 30 comprising scaling circuitry 50 and eight differential amplifiers serving as subtractors 51–58. All six photodetector outputs are input to crosstalk cancellation circuit 30, but scatter signals FS and SS are passed through unchanged. The four fluorescence signals, RR, BR, BY, and BG are input to scaling circuit 50. In addition, a signal RR2, which is signal RR partially corrected for crosstalk, is fed back to scaling circuitry 50 via transit delay 32.

Scaling circuitry 50 generates eight crosstalk correction terms RRR, RRS, BRS, BRR, BRY, BYR, BYG, and BGY. (In the correction term references, the first letter is the laser color, the second letter is the emissions color, and the third letter is the emissions color of the term to be corrected, with S standing for "shadow".) For each output, scaling circuitry 50 defines an input range and a scaling coefficient and constant used to scale inputs across the range. Inputs below the respective range yield a zero output value, while inputs above the respective range yield a value equivalent to that yielded by the top value of the range when scaled. Electrically, the bottom of the range is defined by a threshold input to a comparator, while the top of range is defined by a Zener diode that clips the input signal; the scaling factor is defined by a voltage divider network, and the offset is defined by a capacitance.

In accordance with the present invention, subtractor 51 subtracts from red-excited red photodetector output RR correction term BRS; signal BRS corresponds to a post-pulse generated by a blue-excited red particle at blue laser location LCB. Correction term BRS is set by scaling circuitry 50 to be about 0.3 BR. The subtraction yields signal RR1 which is an interlocation emissions crosstalk corrected version of signal RR.

Signal RR1 is directed from crosstalk cancellation circuit 30 to transit delay 32, which imposes a delay, about 20 $\mu$S, that matches the transit time of a particle flowing from location LCR to location LCB. This delay compensates for the timing misalignment between pulses generated in response to one particle at locations LCR and LCB at two different times. The output RR2 of transit delay 32 is directed to an input of scale circuitry 50 and the plus input of subtractor 52.

Subtractor 52 subtracts from RR2 excitation crosstalk correction term BRR, which is obtained from signal BR by scaling by a factor of about 0.05. All the scaling coefficients are approximate and can be adjusted according to calibration procedures. The difference signal is a crosstalk corrected indication of the APC content of the particle generating pulse RR.

Subtractor 53 subtracts from blue-excited red signal BR intralocation emissions crosstalk term BYR, which is about 0.02, to yield signal BR1. Subtractor 54 subtracts from BR1 inter-location excitation crosstalk term RRR, which is derived by multiplying signal RR2 from transit delay 32 by a factor of about 0.05. This yields signal BR2. In accordance with the present invention, subtractor 55 subtracts signal RRS which is scaled accordingly to the equation 0.33–0.2 RR in the range from 2.0–2.3 Volts. Below RR=2.0 Volts, RRS=0.0 Volts where RR<2.0 Volts; RR=100 mV where RR>2.3 Volts. Note that RRR is time shifted (by transit delay 32) relative to BR, while RRS is not. An RRS pulse thus corresponds to a pre-pulse generated at location LCR and detected at location LCB by an event indicated by a pulse of signal RR.

Subtractor 56 subtracts from blue-excited yellow signal BY intralocation emissions crosstalk term BGY=0.2 BG. The resulting signal BY1 is blue-excited yellow corrected for overlap with the blue-excited green fluorochrome (FITC). Subtractor 57 subtracts from signal BY1 correction term BRY. The contribution of signal BY to BR when RPE is the yellow fluorochrome is negligible, so the scaling factor is 0 and the output indicating PRE is the same as BY1. However, provision for a non-zero coefficient is made to accommodate alternative blue-excited yellow fluorochromes.

Subtractor 58 subtracts from blue-excited green signal BG the intralocation emissions crosstalk term BYG=0.02 BY to provide a crosstalk corrected indication for fluorochrome FITC. Thus, crosstalk cancellation circuitry 30 provides six data signal outputs corresponding to the four fluorochromes and the two scatter signals FS and SS.

These six outputs are input to amplifier bank 34, FIG. 1, which contains six pairs of parallel amplifiers. One amplifier in each pair is linear, the other is logarithmic. A control input determines, for each pair, which amplifier is to be used on the respective throughgoing signal.

The six amplified outputs are directed to pulse processor 36. For each of its six inputs, pulse processor 36 can be set 1) to pass a received pulse, 2) to generate a pulse the peak of which indicates the width of the received pulse, or 3) to generate a pulse the peak of which indicates the area of the received pulse. Pulse processor 36 also imposes a 0.5 $\mu S$ delay, or about 0.25 pulse durations, on each of pulses. This delay is designed to allow the trigger signal to activate six-channel ADC 40 before the leading ends of the pulses arrive. Before they arrive, they pass through peak holder 38 holds pulse peaks so that ADC 40 need only sample once per pulse. Depending on the setting of pulse processor 36, the output of ADC indicates pulse height, pulse width, or pulse area, for each input pulse.

ADC 40 converts the incoming peak data to digital form for transmission to and processing by data processor 22. In the absence of a triggering event, controller 46 disables ADC 40 to minimize data processing and storage requirements.

The six outputs from amplifier bank 34 are also directed to respective inputs of threshold detector 44. For each input, a threshold is set. For each input, threshold detector 44 transmits a binary signal to controller 46 indicating whether the input is below or above threshold. The thresholds are set by controller 46 in accordance with user and/program instructions. Threshold indications can be disabled by setting a maximum value for an input's threshold.

Controller 46 uses the threshold indications for trigger and other timing determinations. Any of the six amplifier outputs can be selected as a trigger by selecting a suitable threshold below maximum. Any combination of amplifier outputs can be selected as a trigger by setting their respective thresholds below maximum. Controller 46 can also use threshold indications to inhibit triggering.

In accordance with the present invention, controller 46 can raise the threshold of the blue-excited red channel for the duration that a red-excited red pulse is above a 2.0 Volt threshold. This effectively gates a pre-pulse out of the triggering loop. This gating is a severe form of crosstalk cancellation. It ensures against false triggering at the expense of ignoring coincidence of a pre-pulse and real pulse being detected by the blue-excited red detector. This trigger gating approach can still permit triggering along another channel, e.g., the blue-excited yellow channel so that some coincidences are not excluded from triggering.

The gating approach makes sense where the interlocation emissions crosstalk cancellation is optimized for quantization and is not biased enough against false triggering; the quantization data is available, but the gating prevents the false triggering.

Of course, as is true for the preferred crosstalk compensation, the gating can be applied to the other detection channels, e.g., the red-excited red channel to prevent triggering on post-pulses. Gating and subtraction are limited to cases where the trigger is to be blue-excited red under logarithmic amplification and where red laser LZR is on. In one embodiment of the invention, gating is not used, but interlocation emissions crosstalk cancellation by subtraction is used when these three conditions are met.

Controller 46 can perform a number of functions in accordance with user/program input. On command, controller 46 can calibrate transit delay 32 by comparing the threshold indications from photodetector DRR the APC and from any of the blue-excited detectors. Controller 46 is coupled to transit delay 32 for adjusting the delay imposed thereby. Controller 46 can adjust the functions applied by scale circuitry 50 of crosstalk cancellation circuitry 30. Alternatively, the crosstalk cancellation or other subtractions can be hardwired and thus not be adjustable. Controller 46 controls selection of logarithmic versus linear amplification according to user/program input. Controller 46 provides control signals to pulse processor 36 to determine for each channel whether peak height, width, or area is to be indicated. Controller 46 provides the timing to enable the conversion of the held peak signals by ADC 40.

Data processor 22 does the final tabulation and analysis of the data received from pulse processor 20. In some cases, crosstalk corrections are optimized to prevent false triggering rather than for data analysis. For data analysis, data processor 22 can correct for non-optimal crosstalk cancellation.

The method M1 implemented by flow cytometry system AP1 is flow charted in FIG. 3. Step S1 involves illuminating the two flow path locations respectively with red and blue laser light. Step S2 involves flowing sample cells, or other particles, past the two locations. Step S3 involves detecting red fluorescence at both locations. Step S4 involves canceling interlocation emission crosstalk from the detection from at least one of the locations. Step S5 involves applying the crosstalk corrected signal for triggering purposes and/or using the corrected signal as data to be used in characterized the sample.

While preferred embodiments of the invention have been described, those skilled in the art can apply the description to enable them to practice the invention a variety of ways. While in the described embodiment, the blue laser is downstream of the red laser, the invention is equally applicable with the red laser downstream; in this case, additional delay lines may be required in the electronic path of the upstream photodetectors. While the described embodiment is a dual-laser system, the invention is more essential in systems with three or more lasers.

In the described embodiment, gating of potential trigger pulses is achieved at the threshold detector. Alternatively, gating can be achieved at the amplifiers or electronically upstream thereof. In these cases, the gating may apply to the data path as well as the trigger path. Alternatively, crosstalk cancellation can be performed separately for trigger bound and data bound pulses; in other words, detection pulses can be duplicated and crosstalk corrected in parallel. This would allow different crosstalk coefficients to be applied to trigger and data pulse streams—allowing independent optimization for both. While in the preferred embodiment, scaling and subtraction are used to compensate for crosstalk cancellation, other embodiments apply non-linear crosstalk cancellation.

If gating is employed, it is important that the real and the shadow detections be distinguished. Otherwise, a shadow pulse could be used as a trigger or data, while a real event is ignored. To this end, a comparator can be used to compare the outputs of the two red fluorescent detectors to determine which has the stronger output. The weaker output is presumed to be the shadow, which is then gated for the duration of the other pulse.

The described embodiments correct for crosstalk in the analog domain. Where ample data processing power is available, the photodetector outputs can be converted to the digital domain without prior crosstalk correction. The present invention provides for crosstalk correction in the digital domain. These and other modifications to and variations up the described embodiments are provided for by the present invention, the scope of which is limited only by the following claims.

What is claimed is:

1. A particle analyzer comprising:

flow means for flowing particles, including a first particle type and a second particle type, through a first location and through a second location;

first illumination means for illuminating said particles at said first location with light having a first spectral distribution;

second illumination means for illuminating said particles at said second location with light having a second spectral distribution different from said first spectral distribution;

first detection means for generating a first indicator when a particle of said first particle type is at said first location;

second detection means for generating a second indicator when a particle of said second particle type is at said second location, said second detection means also providing a third indicator when a particle of said first particle type is at said first detection location; and cancellation means for at least partially canceling said third indicator in response to generation of said first indicator.

2. An analyzer as recited in claim 1 wherein said first particle type fluoresces when excited by illumination having said first spectral distribution, wherein said second particle type fluoresces when excited by illumination having said second spectral distribution, and wherein said second detection means detects fluorescence from said particle of said second type when it is at said second location, said second detection means also detecting fluorescence from said particle of said first type when it is at said first location.

3. A particle analyzer as recited in claims 1 wherein said second detection means transmits said second and third indicators along a channel, said first indicator having a duration, said cancellation means canceling said third indicator by gating said channel for said duration of said first indicator.

4. A particle analyzer as recited in claim 1 wherein said cancellation means cancels said third indicator by subtracting therefrom a fourth indicator derived from said first indicator.

5. A particle analyzer as recited in claim 1 wherein said particles have a transit time between said first and second locations, said second detection means having an output including said second and third indicators, said canceling means subtracting from said output a concurrent indicator derived from said first indicator and a time-shifted indicator derived from said first indicator and time-shifted relative to said concurrent indicator by said transit time.

6. A method of analyzing particles, including particles of a first type and particles of a second type, said method comprising the steps of:

flowing said particles through a first detection location illuminated by light of a first spectral distribution and through a second detection location illuminated by light of a second spectral distribution different from said first spectral distribution;

generating a first indication when a particle of said first type is at said first detection location, generating a second indication along a second channel when a particle of said second type is at said second detection location, and generating a third indication along said second channel when said particle of said first type is at said first detection location; and at least partially canceling said third indicator in response to said first indicator.

7. A method as recited in claim 6 wherein particles of said first type fluoresce when excited by illumination of said first spectral distribution and particles of said second type fluoresce when excited by illumination of said second spectral distribution, said generating step including detecting fluorescence from a particle of said first particle type at said second location.

8. A method as recited in claim 6 wherein said second and third indictors are transmitted along a channel, said first indicator having a duration, said canceling step involving gating said channel for said duration.

9. A method as recited in claim 6 wherein said canceling step involves subtracting from said third indicator a fourth indicator derived from said first indicator.

10. A method as recited in claim 9 wherein said particles have a transit time between said first and second locations, said generating step involving generating an output including said second and third indicators, said canceling step involving subtraction from said output a concurrent indicator and a time-shifted indicator, said concurrent indicator being derived from said first indicator, said time-shifted indicator being derived from said first indicator and time-shifted by said transit time relative to said concurrent indicator.

11. A particle analyzer comprising:

flow means for flowing particles, including a first particle, through a first location and through a second location;

first illumination means for illuminating said particles at said first location;

second illumination means for illuminating said particles at said second location;

first detection means for generating a first indicator when said first particle is at said first location;

second detection means for generating a second indicator when said first particle is at said second location; and cancellation means for at least partially canceling crosstalk in said first indicator and generated when said first particle is at said second location.

12. A particle analyzer comprising:

flow means for flowing particles through a first location and through a second location;

first illumination means for illuminating said first location with light having a first source spectral distribution;

second illumination means for illuminating said second location with light having a second source spectral distribution different from said first source spectral distribution;

first detection means for generating a first indicator when light of a first emissions spectral distribution is emitted from said first location;

second detection means for generating a second indicator when light of a second emissions spectral distribution is emitted from said second location, said second detection means also providing a third indicator when light of a third emissions spectral distribution is emitted from said first location; and cancellation means for at least partially canceling said third indicator in response to generation of said first indicator.

13. A method of analyzing particles, including a first particle, said method comprising the steps of:

flowing said particles through a first illuminated detection location and through a second illuminated detection location;

generating a first indication when said first particle is at said first detection location, generating a second indication along a second channel when said first particle is at said second detection location; and at least partially canceling crosstalk generated at said second location when said particle is at said first location.

* * * * *